(12) United States Patent
Kang et al.

(10) Patent No.: US 10,394,012 B2
(45) Date of Patent: Aug. 27, 2019

(54) ENDOSCOPY SYSTEM

(71) Applicant: INTHESMART Inc., Seoul (KR)

(72) Inventors: Uk Kang, Seoul (KR); Ilhyung Shin, Jeju (KR)

(73) Assignee: INTHESMART Inc., Seoul (KR)

( * ) Notice: Subject to any disclaimer, the term of this patent is extended or adjusted under 35 U.S.C. 154(b) by 280 days.

(21) Appl. No.: 15/335,462

(22) Filed: Oct. 27, 2016

(65) Prior Publication Data
US 2017/0285323 A1 Oct. 5, 2017

(30) Foreign Application Priority Data

Apr. 1, 2016 (KR) .......................... 10-2016-0040028
Jun. 24, 2016 (KR) .......................... 10-2016-0079112

(51) Int. Cl.
| G02B 23/24 | (2006.01) |
| A61B 1/00 | (2006.01) |
| A61B 1/04 | (2006.01) |
| A61B 1/06 | (2006.01) |
| A61B 1/07 | (2006.01) |

(Continued)

(52) U.S. Cl.
CPC ...... *G02B 23/2461* (2013.01); *A61B 1/00006* (2013.01); *A61B 1/00009* (2013.01); *A61B 1/00025* (2013.01); *A61B 1/00045* (2013.01); *A61B 1/00057* (2013.01); *A61B 1/04* (2013.01); *A61B 1/0669* (2013.01); *A61B 1/0684* (2013.01); *A61B 1/07* (2013.01); *F21V 5/045* (2013.01); *F21V 23/0457* (2013.01); *G02B 23/2484* (2013.01); *G02B 23/26* (2013.01); *H04N 5/2256* (2013.01); *H04N 2005/2255* (2013.01)

(58) Field of Classification Search
CPC . G02B 23/2461; F21V 5/045; A61B 1/00025; A61B 1/00045; A61B 1/04
See application file for complete search history.

(56) References Cited

U.S. PATENT DOCUMENTS

| 8,698,884 B2 | 4/2014 | Godo | |
| 2010/0016664 A1* | 1/2010 | Viola | ................. A61B 17/3423 |
| | | | 600/114 |

(Continued)

FOREIGN PATENT DOCUMENTS

| JP | 09-129018 | 5/1997 |
| JP | 2004-275542 A | 10/2004 |

(Continued)

*Primary Examiner* — Evan P Dzierzynski
(74) *Attorney, Agent, or Firm* — Patent Office of Dr. Chung Park

(57) ABSTRACT

The present disclosure relates to an endoscopy system. The endoscope system includes: a first light source unit which is installed on a substrate; a second light source unit which is installed on the substrate and which emits light when the first light source unit does not emit light; an optical unit through which the light of the first light source unit or the second light source unit passes; a light guide unit which induces the light which passed through the optical unit to the inside of a target object; an image sensing unit which senses the light reflected and reached from the target object and which converts the sensed light into an image signal; and an image signal processing unit which processes the image signal to display on a display unit.

12 Claims, 13 Drawing Sheets

(51) Int. Cl.
    *F21V 5/04*   (2006.01)
    *F21V 23/04*  (2006.01)
    *G02B 23/26*  (2006.01)
    *H04N 5/225*  (2006.01)

(56) References Cited

U.S. PATENT DOCUMENTS

| | | | | |
|---|---|---|---|---|
| 2011/0175536 A1* | 7/2011 | Fujita | ............ | F21S 8/02 |
| | | | | 315/185 R |
| 2013/0063051 A1* | 3/2013 | Sterling | ............ | B25F 5/021 |
| | | | | 315/360 |
| 2013/0193875 A1* | 8/2013 | Godo | ............ | A61B 1/0684 |
| | | | | 315/297 |
| 2013/0200794 A1* | 8/2013 | Lin | ............ | H05B 33/0809 |
| | | | | 315/86 |
| 2015/0099932 A1* | 4/2015 | Morimoto | ............ | H05B 33/0854 |
| | | | | 600/180 |
| 2017/0194302 A1* | 7/2017 | Disney | ............ | H01L 33/62 |

FOREIGN PATENT DOCUMENTS

| | | |
|---|---|---|
| JP | 2005-328883 A | 12/2005 |
| JP | 2006-136519 A | 6/2006 |
| KR | 10-2007-0071556 A | 7/2007 |

* cited by examiner

[Fig. 1]
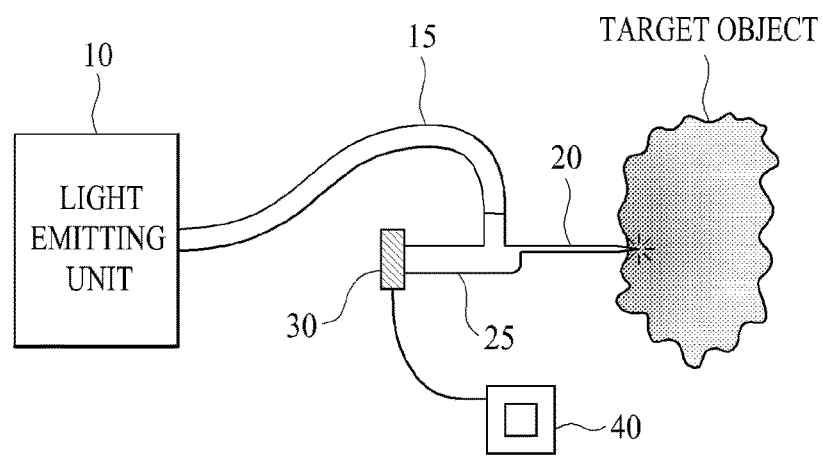
[Fig. 2]
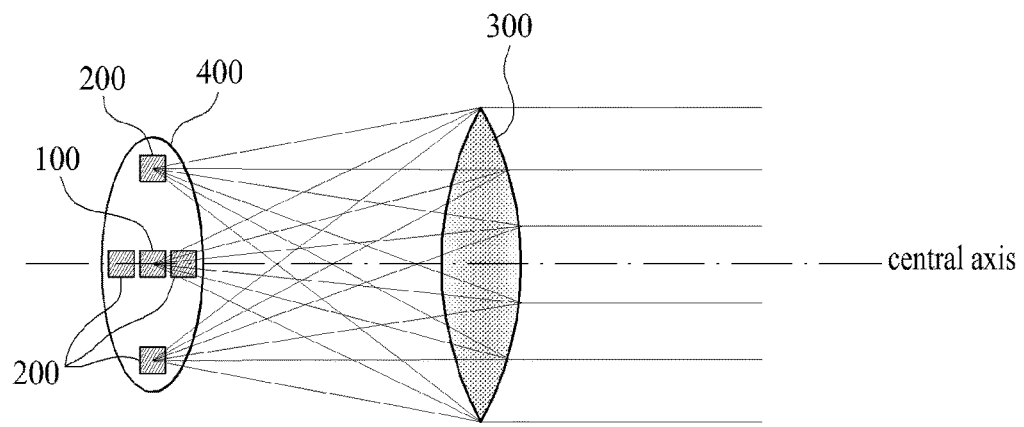

[Fig. 3]
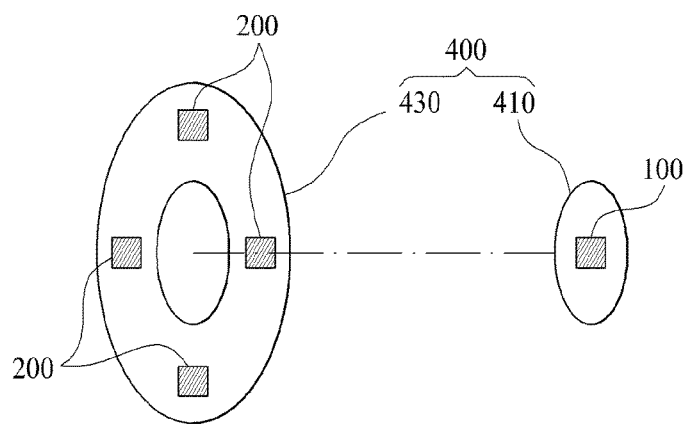
[Fig. 4]
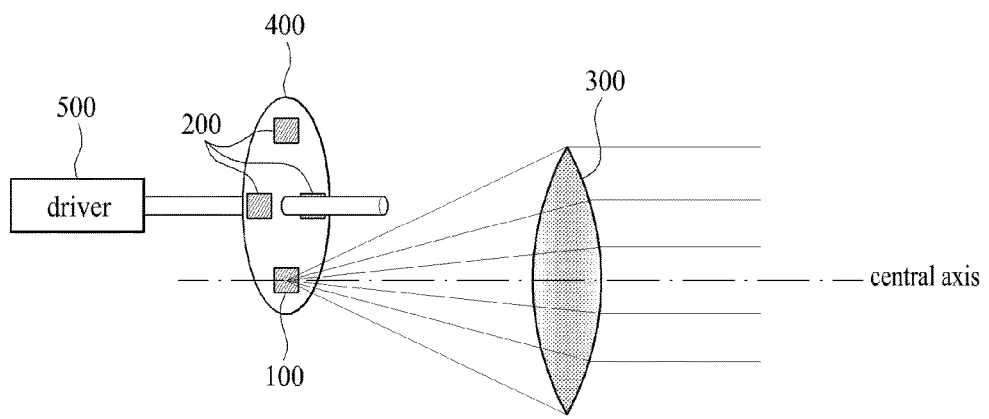

[Fig. 5]
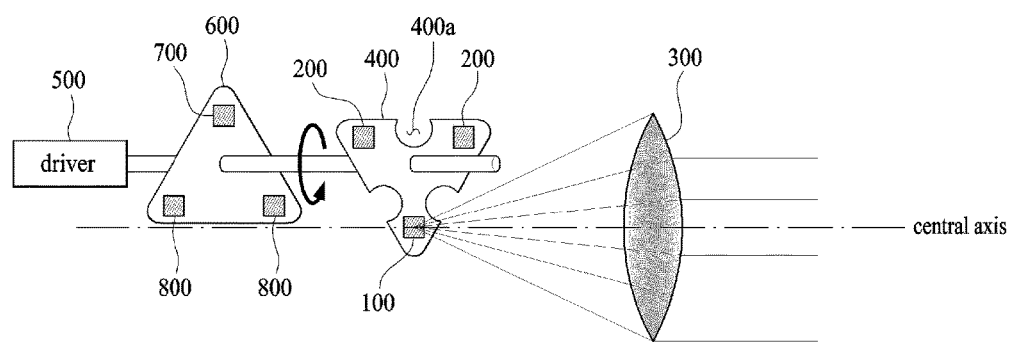
[Fig. 6]
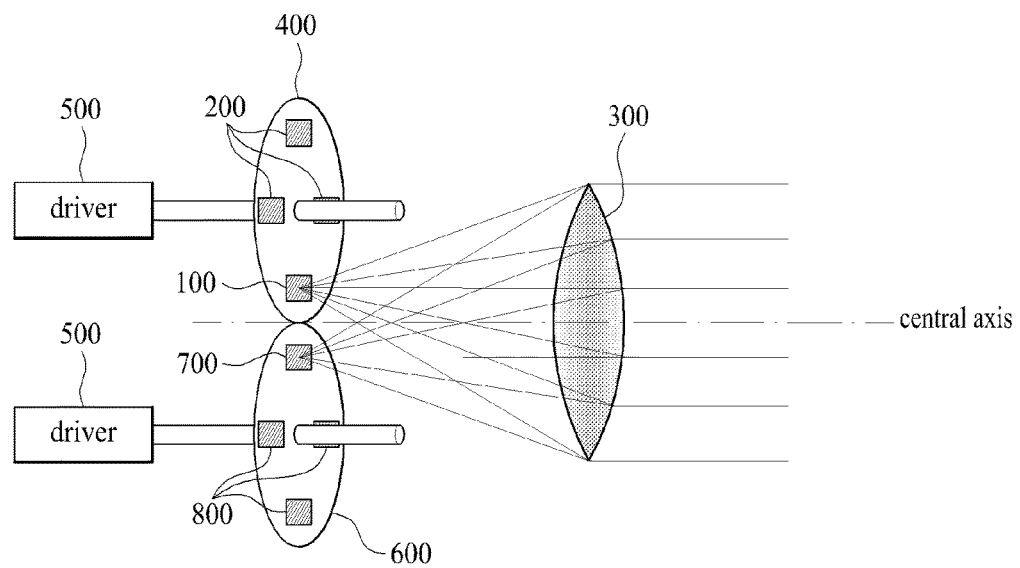

[Fig. 7]
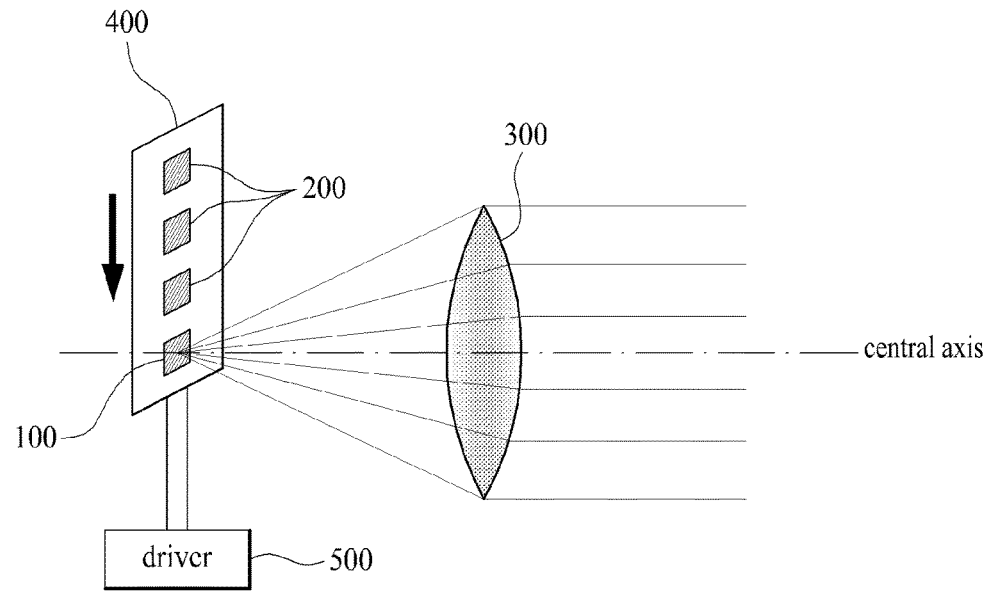
[Fig. 8]
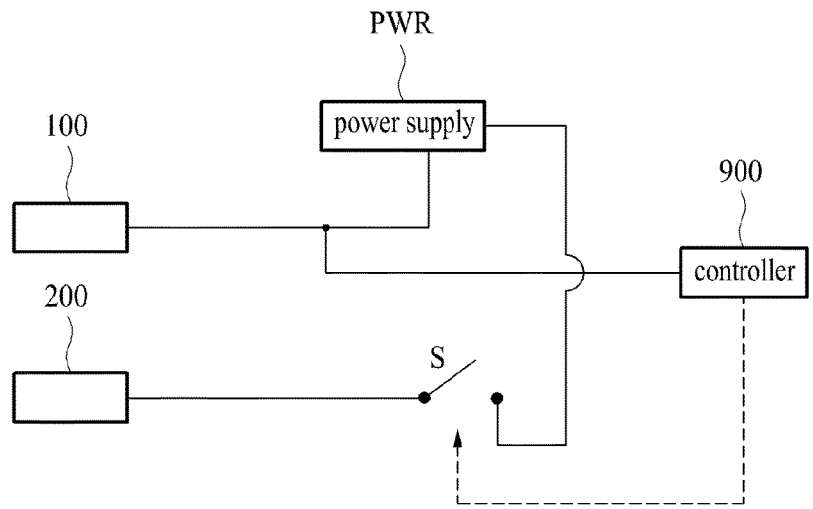

[Fig. 9]
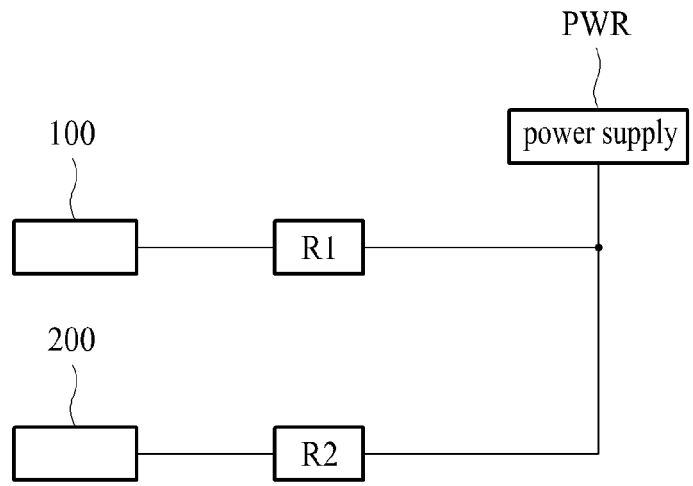
[Fig. 10]
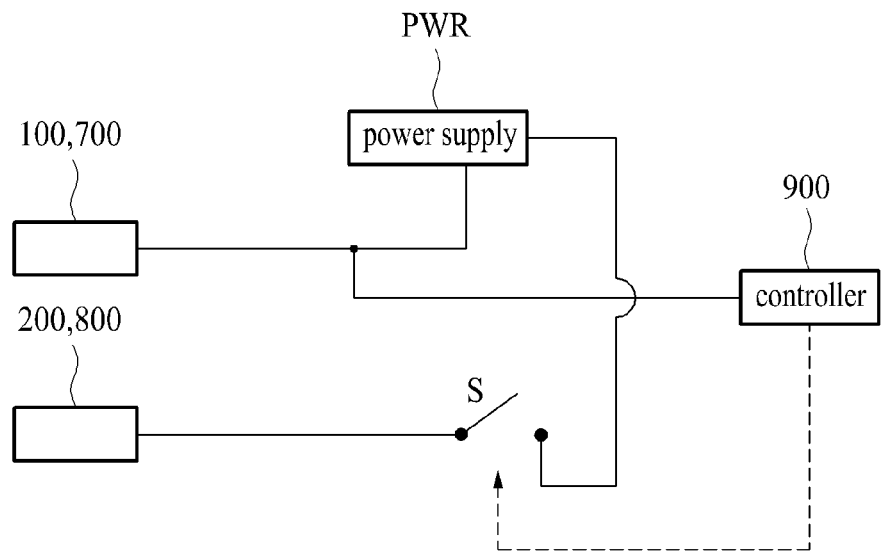

[Fig. 11]
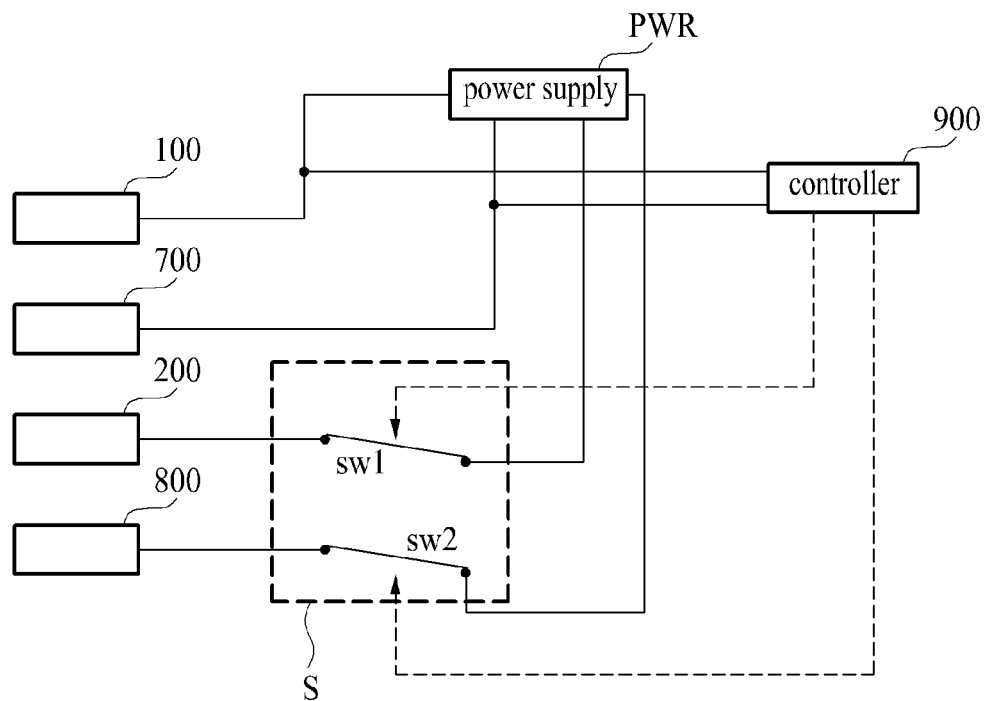
[Fig. 12]
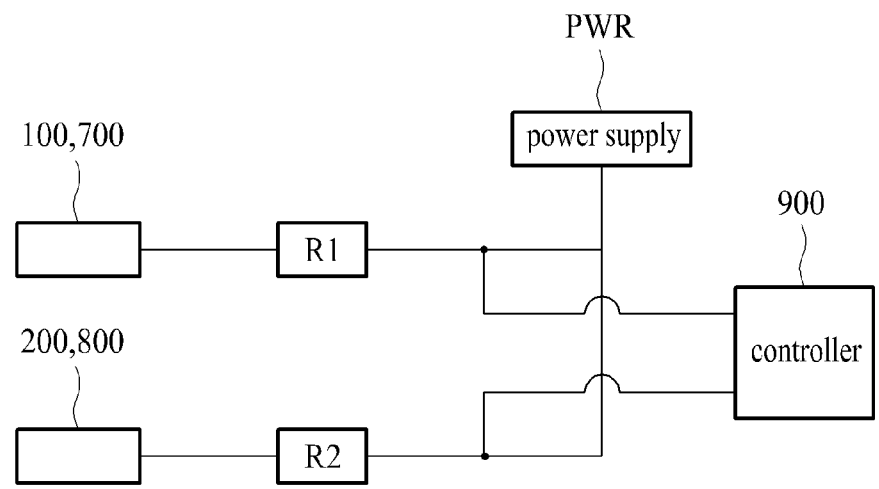

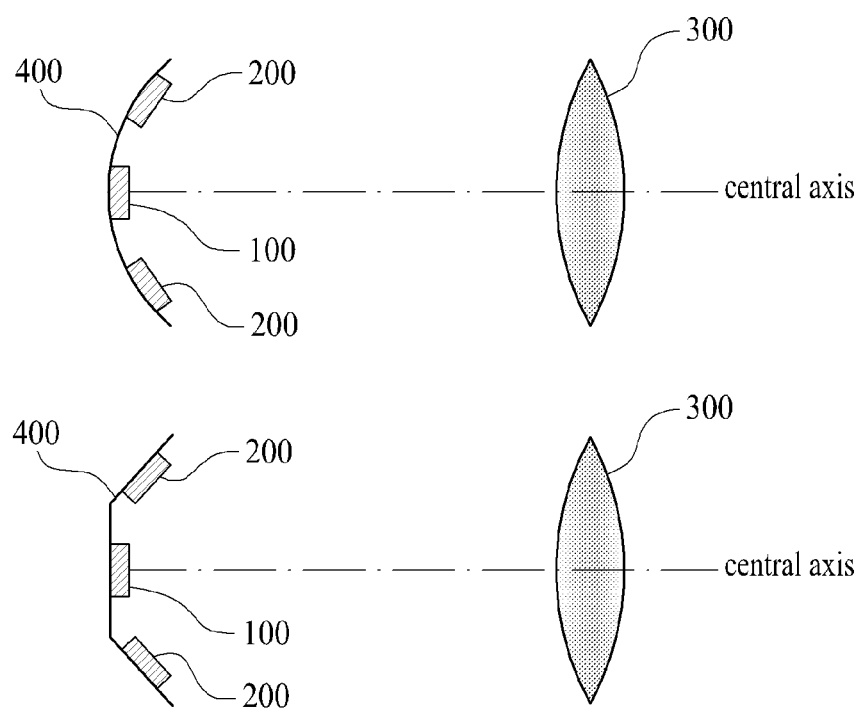
[Fig. 13]

[Fig. 14]
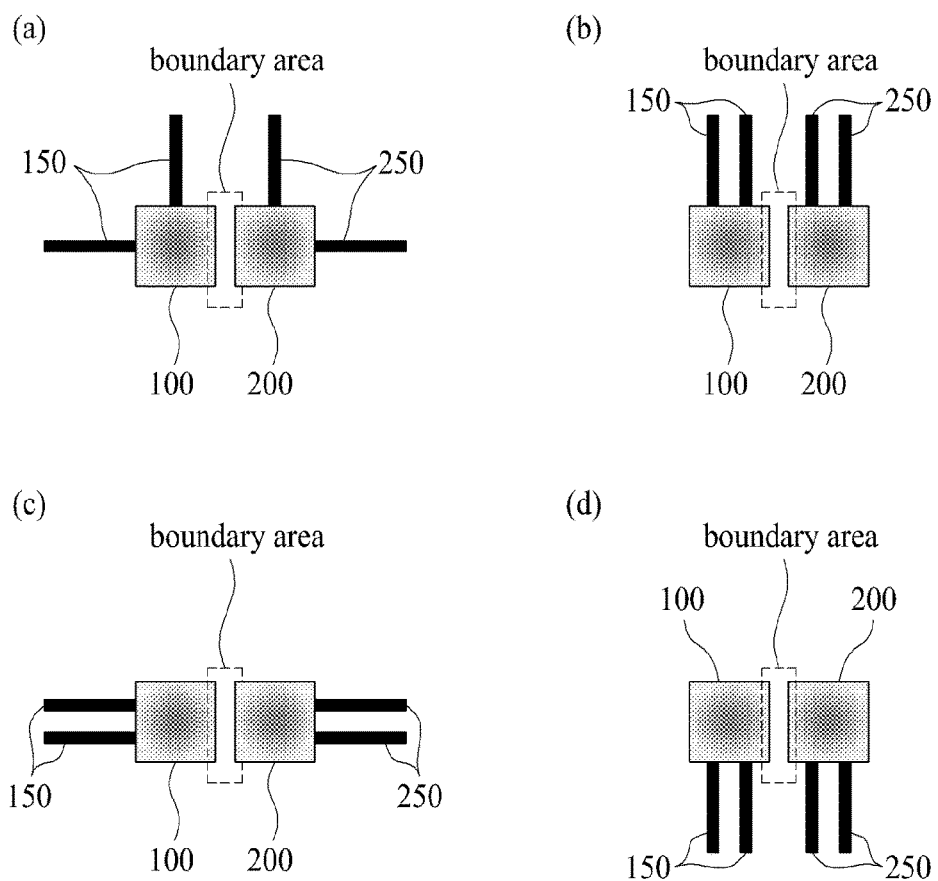

[Fig. 15]
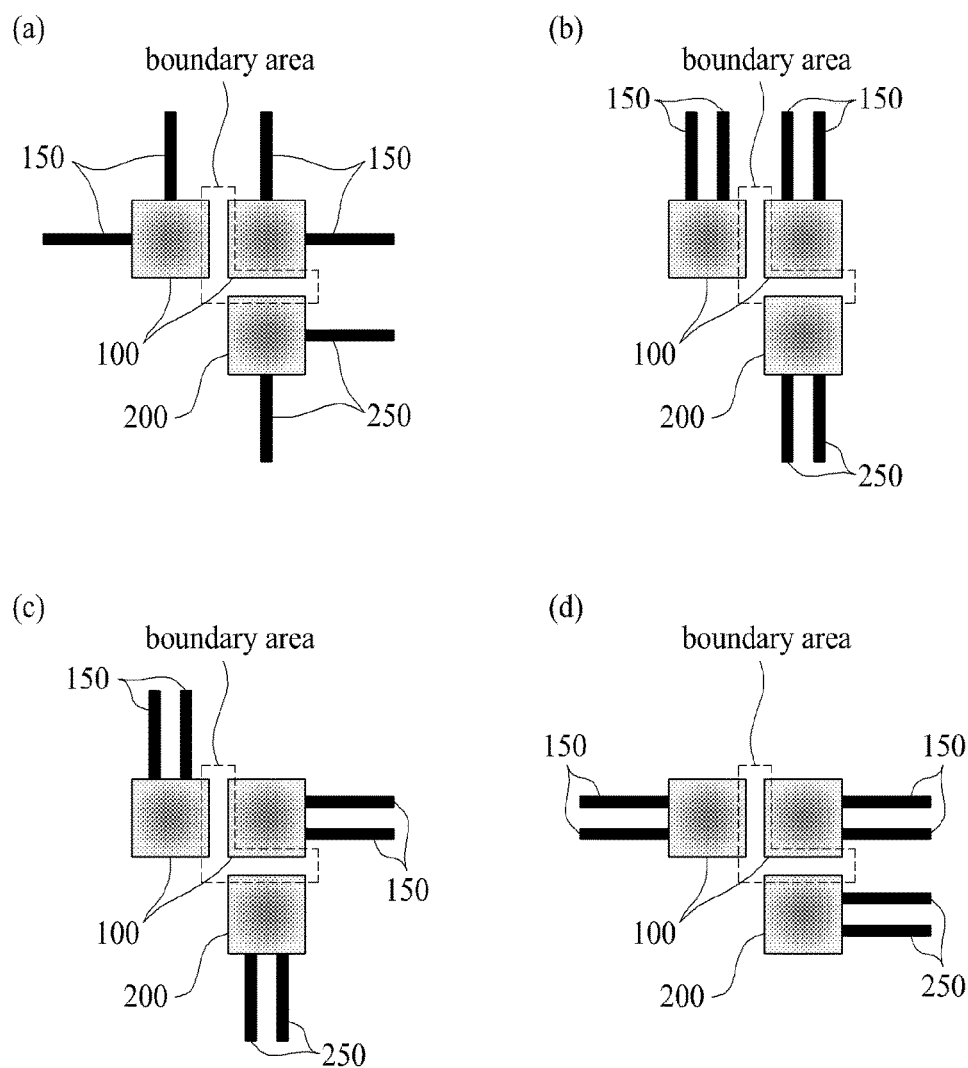

[Fig. 16]
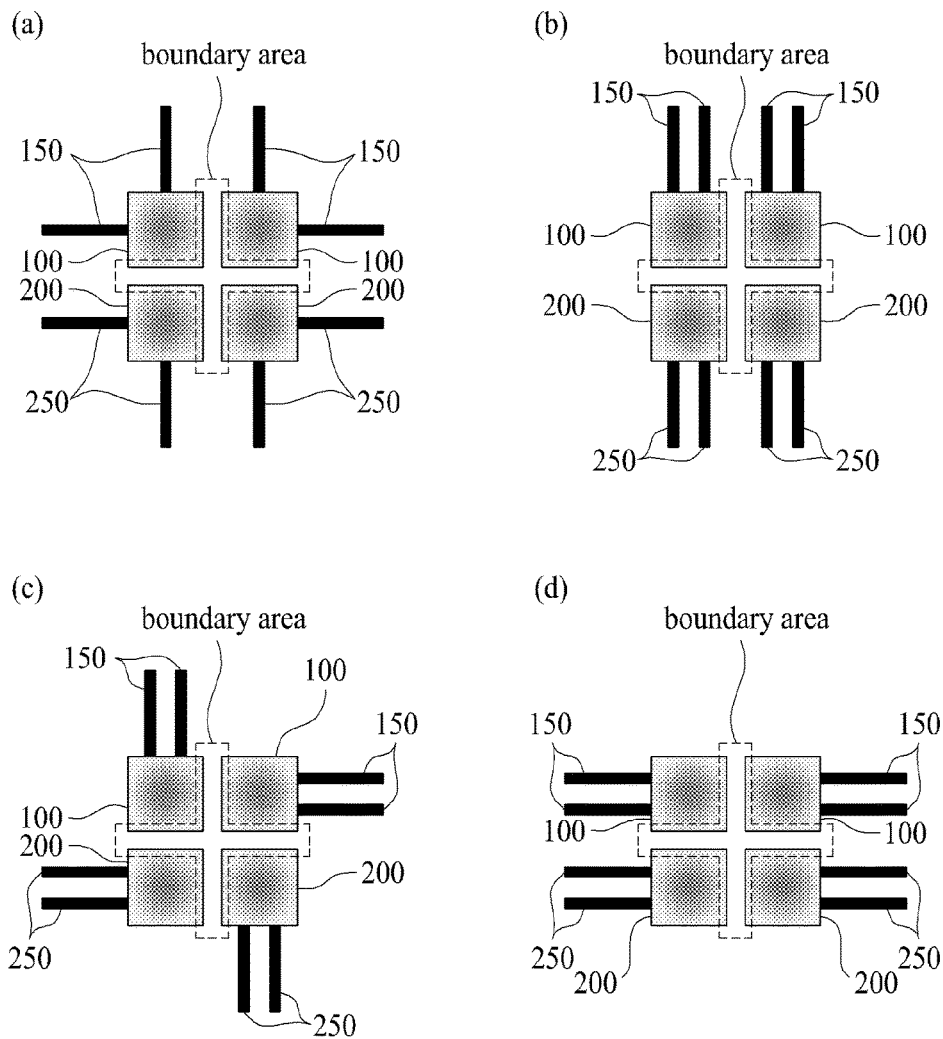

[Fig. 17]
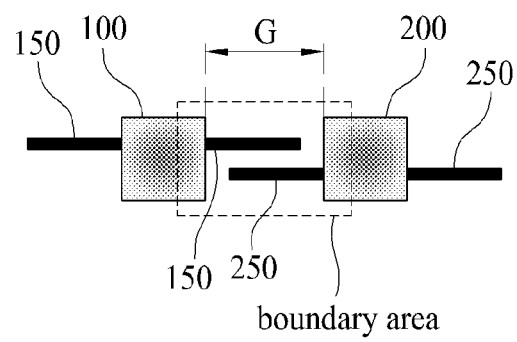
[Fig. 18]
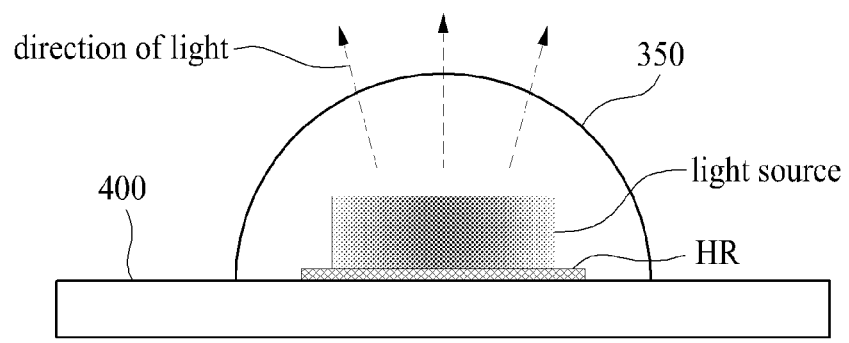

[Fig. 19]
(a) 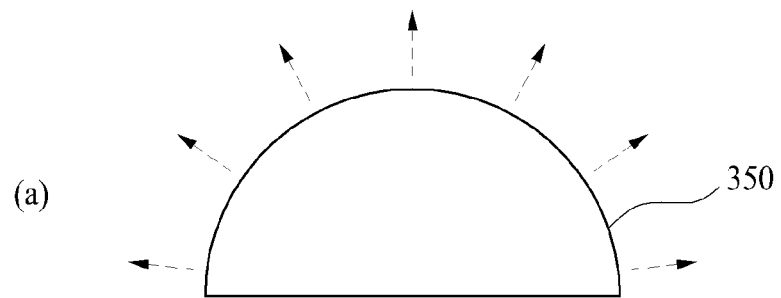
(b) 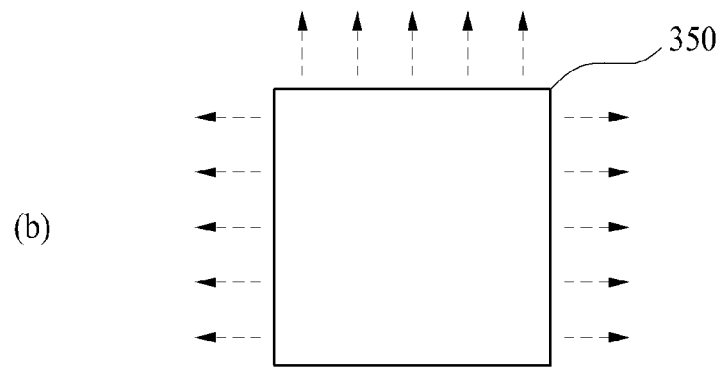
(c) 

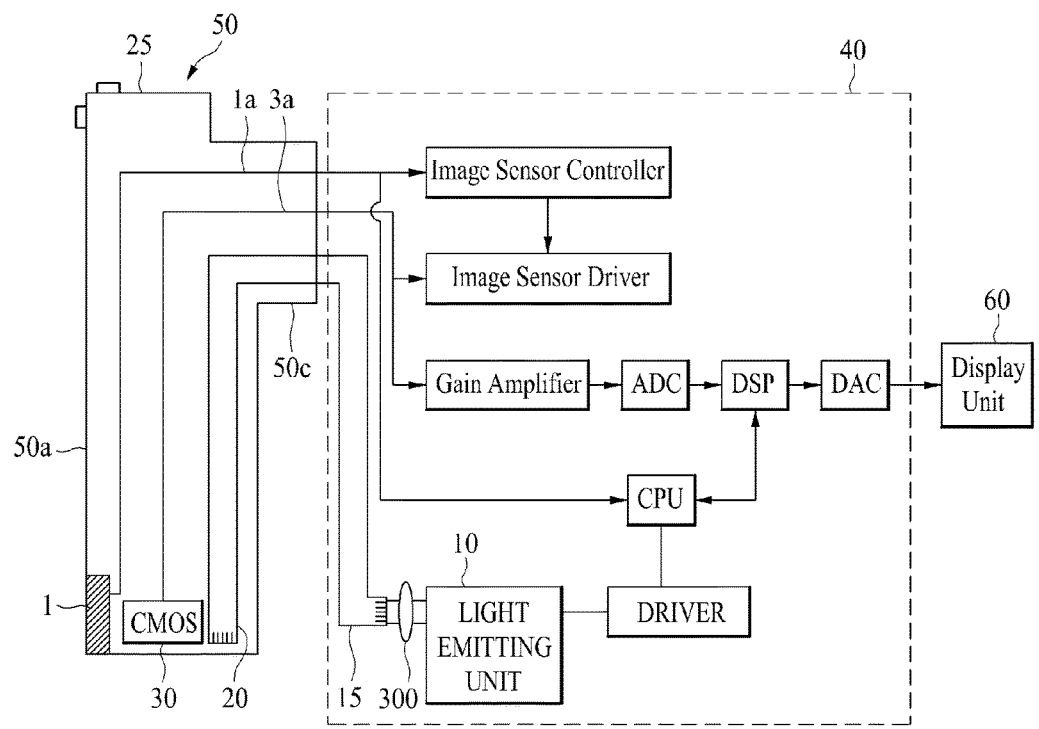
[Fig. 20]

ENDOSCOPY SYSTEM

CROSS-REFERENCE TO RELATED APPLICATIONS

This application claims priority under 35 U.S.C. § 119 from Korean Application No. 10-2016-0040028 filed on Apr. 1, 2016 and Korean Application No. 10-2016-0079112 filed on Jun. 24, 2016, the subject matter of which is incorporated herein by reference.

BACKGROUND OF THE INVENTION

Field of the Invention

The present disclosure relates to an endoscopy system.

Description of the Related Art

An endoscope system requires a high degree of stability as it is used for medical internal check. The endoscopic system emits a light to the inside of a target object and senses a reflected light to generate a corresponding image of the inside of the target object.

At this time, when a light source is unable to emit light as it does not work reliably, it is not possible to achieve an image generation, such that a user who uses the endoscope system may not accomplish a medical care or a medical checkup smoothly.

Accordingly, a research on an endoscopy system is progressed to perform a stable operation even if the light source does not operate normally.

SUMMARY OF THE INVENTION

The present disclosure has been made in view of the above problems, and provides an endoscopic system to generate an image stably even if a light source does not operate normally.

In accordance with an aspect of the present disclosure, an endoscope system includes: a first light source unit which is installed on a substrate; a second light source unit which is installed on the substrate and which emits light when the first light source unit does not emit light; an optical unit through which the light of the first light source unit or the second light source unit passes; a light guide unit which induces the light which passed through the optical unit to the inside of a target object; senses the light reflected and reached from the target object and which converts the sensed light into an image signal; and an image signal processing unit which processes the image signal to display on a display unit. The light of the second light source unit passes through the optical unit when the light of the first light source unit does not emit light. The first light source unit is arranged along a central axis of the optical unit, and the second light source unit is arranged to deviate the central axis. The endoscope system further includes a controller which senses whether power is supplied to the first light source unit, and the controller turns a switching unit on by sensing a stop of the supply of the power to supply the power to the second light source unit, when the power is not supplied to the first light source unit. The first light source unit that is supplied with power to emit light is connected to a first resistor and the second light source unit is connected to a second resistor, the first resistor has a small resistance value in comparison with the second resistor, and the power is supplied to the second light source unit through the second resistor when the first light source unit does not emit light.

In accordance with another aspect of the present disclosure, an endoscope system includes: a first light source unit and a second light source unit which are installed on a substrate; an optical unit through which a light of the first light source unit passes; a driver which moves the substrate so that a light of the second light source unit passes through the optical unit when the first light source unit does not emit light; a light guide unit which induces the light of the first light source unit and the second light source unit which passed through the optical unit to the inside of a target object; an image sensing unit which senses the light reflected and reached from the target object and which converts the sensed light into an image signal; and an image signal processing unit which processes the image signal to display on a display unit. The first light source unit is arranged along the optical unit and a central axis when the first light source unit emits light, and the driver rotates the substrate so that the second light source unit is arranged along the optical unit and the central axis when the first light source unit does not emit light. The endoscope system further includes an additional substrate, and a third light source unit and a fourth light source unit installed on the additional substrate, and the driver moves the additional substrate so that a light of the fourth light source unit passes through the optical unit when the third light source unit does not emit light. The light of the third light source unit and the fourth light source unit passes through the optical unit through a groove or a hole formed in the substrate. The first light source unit and the third light source unit that emit light are located closer to the central axis of the optical unit in comparison with the second light source unit and the fourth light source unit respectively, and the driver rotates the substrate when the first light source unit does not emit light so that the second light source unit is positioned to be close to the central axis in comparison with the first light source unit, and rotates the substrate when the third light source unit does not emit light so that the fourth light source unit is positioned to be close to the central axis in comparison with the third light source unit. The first light source unit and the third light source unit emit a light of a different wavelength simultaneously, and, when the first light source unit and the third light source unit does not emit light, the second light source unit and the fourth light source unit emit a light of a different wavelength simultaneously. The first light source unit is arranged along the optical unit and the central axis when the first light source unit emits light, and the driver moves the substrate linearly so that the second light source unit is arranged along the optical unit and the central axis when the first light source unit does not emit light. The endoscope system further includes a controller which senses a stop of a supply of a power to at least one of the first light source unit and the third light source unit, and the controller controls a switching unit to supply power to the second light source unit when a supply of a power to the first light source unit is stopped, and to supply power to the fourth light source unit when a supply of a power to the third light source unit is stopped. The first light source unit and the third light source unit are connected to a first resistor and the second light source unit and the fourth light source unit are connected to a second resistor, the first resistor has a small resistance value in comparison with the second resistor, and a power is supplied to the second light source unit and the fourth light source unit through the second resistor when the first light source unit and the third light source unit are unable to emit light.

In accordance with another aspect of the present disclosure, an endoscope system includes: a first light source unit which is installed on a substrate, and which is provided with a first terminal; a second light source unit which is installed on the substrate and which is provided with a second terminal in a non-boundary area which is not a boundary area with the first light source unit to emit light when the first light source unit does not emit light; an optical unit through which the light of the first light source unit or the second light source unit passes; a light guide unit which induces the light which passed through the optical unit to the inside of a target object; an image sensing unit which senses the light reflected and reached from the target object and which converts the sensed light into an image signal; and an image signal processing unit which processes the image signal to display on a display unit. The first light source unit and the second light source unit include total n partial light sources, and, when the first light source unit includes m (m<n, m and n is a natural number) partial light sources, the second light source unit includes partial light source which is equal to or greater than one and equal to or less than n−m. The first light source unit is arranged along a central axis of the optical unit, and the second light source unit is arranged to deviate the central axis. The first light source unit and the second light source unit further include an additional optical unit covering a light source mounted on the substrate, and a cross-sectional shape of the additional optical unit is curved or flat with respect to a direction of a light. The first light source unit and the second light source unit further include an additional optical unit covering a light source mounted on the substrate, and the additional optical unit performs a function of a Fresnel lens.

BRIEF DESCRIPTION OF THE DRAWINGS

The objects, features and advantages of the present disclosure will be more apparent from the following detailed description in conjunction with the accompanying drawings, in which:

FIG. 1 illustrates an implementation of an endoscope system according to an embodiment of the present disclosure;

FIG. 2 and FIG. 3 illustrate an endoscope system according to a first embodiment of the present disclosure;

FIG. 4 and FIG. 7 illustrate an endoscope system according to a second embodiment of the present disclosure;

FIG. 5 and FIG. 6 illustrate a modification of the endoscope system according to the second embodiment of the present disclosure;

FIG. 8 and FIG. 9 illustrate an operation of a controller of the endoscope system according to the first embodiment of the present disclosure;

FIG. 10 to FIG. 12 illustrate an operation of a controller of the endoscope system according to the second embodiment of the present disclosure;

FIG. 13 illustrates a cross-sectional shape of a substrate;

FIG. 14 to FIG. 16 illustrate a first light source unit and a second light source unit of an endoscope system according to a third embodiment of the present disclosure;

FIG. 17 illustrates a comparative example of the endoscope system according to the third embodiment of the present disclosure;

FIG. 18 illustrates a cross-section of the first light source unit and the second light source unit;

FIG. 19 illustrates an additional optical unit; and

FIG. 20 is a block diagram illustrating an endoscope system according to embodiments of the present disclosure.

DETAILED DESCRIPTION OF EXEMPLARY EMBODIMENTS

Exemplary embodiments of the present disclosure are described with reference to the accompanying drawings in detail. The same reference numbers are used throughout the drawings to refer to the same or like parts. Detailed descriptions of well-known functions and structures incorporated herein may be omitted to avoid obscuring the subject matter of the present disclosure.

The terms and words used in the following description and claims are not limited to the bibliographical meanings, but, are merely used by the inventor to enable a clear and consistent understanding of the present disclosure. It is to be understood that the singular forms "a," "an," and "the" include plural referents unless the context clearly dictates otherwise.

In the present disclosure, the terms such as "include" and/or "have" may be construed to denote a certain characteristic, number, step, operation, constituent element, component or a combination thereof, but may not be construed to exclude the existence of or a possibility of addition of one or more other characteristics, numbers, steps, operations, constituent elements, components or combinations thereof.

FIG. 1 illustrates an implementation of an endoscope system according to an embodiment of the present disclosure.

Referring to FIG. 1, the endoscope system according to an embodiment of the present disclosure may include a light emitting unit 10, a light guide unit 20, an image sensing unit 30, and an image signal processing unit 40.

The light emitting unit 10 may emit light of various wavelengths such as visible light, ultraviolet rays, and infrared rays.

The configuration of the light emitting unit 10 is described in more detail later.

The light guide unit 20 may derive the light generated by the light emitting unit 10 to the inside of a target object. The target object may be a person, an animal, a product, or the like, but it is not limited thereto.

The image sensing unit 30 may sense the light which is reflected from the target object and convert the sensed light into an image signal. To this end, the image sensing unit 30 may include a charge-coupled device (CCD) or a complementary metal oxide semiconductor (CMOS), but it is not limited thereto.

The image signal processing unit 40 may process the image signal to display on a display unit (not shown) such as a monitor or TV.

Next, the endoscope system according to an embodiment of the present disclosure is described with reference to the drawings. In the following drawings, the light emitting unit 10 is mainly shown for the convenience of explanation. The light emitting unit 10 may include a first light source unit 100 and a second light source unit 200, and may further include a third light source unit 700 and a fourth light source unit 800.

As shown in FIG. 2, the endoscope system according to a first embodiment of the present disclosure may include the first light source unit 100, the second light source unit 200, an optical unit 300, and the light guide unit 20.

The first light source unit 100 may be installed on a substrate 400.

The second light source unit 200 may be installed on the substrate 400 and emit light when the first light source unit 100 does not emit light. At this time, the second light source unit 200 may be installed close to the first light source unit 100, but it is not limited thereto. In FIG. 2, the number of the second light source unit 200 is four, but it is not limited thereto and may be equal to or greater than one.

The first light source unit 100 and the second light source unit 200 may include an LED, but it is not limited thereto. In FIG. 2, it is illustrated that the first light source unit 100 and the second light source unit 200 include a single LED but may include a plurality of LEDs. In addition, in the following drawings, it is illustrated that the first light source unit 100 and the second light source unit 200 include a single LED but may include a plurality of LEDs.

The first light source unit 100 and the second light source unit 200 may, as if a white light, emit light of various wavelengths such as visible light, ultraviolet rays, and infrared rays.

The light of the first light source unit 100 or the second light source unit 200 may pass through the optical unit 300. At this time, a central axis may be a central axis 300 of the optical unit 300.

At this time, the optical unit 300 may include a collimator, but it is not limited thereto, and may include various lenses according to the needs of design.

The installation location of the optical unit 300 may be installed in an area where the light emitting unit 10 and an optical fiber 15 are connected, but it is not limited thereto. The optical fiber 15 may provide a path where a light passed through the optical unit 300 progresses to the light guide unit 20.

To this end, the optical fiber 15 may be connected to a handle 25, and the handle 25 may be connected to the light guide unit 20, but it is not limited to this structure. A doctor or an operator may operate the endoscope system according to an embodiment of the present disclosure through the handle 25.

The light guide unit 20 may guide a light passed through the optical unit 300 into the inside of the target object.

As this time, as shown in FIG. 2, when the light of the first light source unit 100 is not emitted, the light of the second light source unit 200 may pass through the optical unit 300 in the state in which the substrate 400 does not move at all.

Thus, the second light source unit 200 may emit light when the first light source unit 100 does not emit light due to failure after emitting light, such that it is possible to accomplish a stable operation of the endoscope system.

For example, when a doctor performs a treatment or a surgery through a general endoscope system, if a light is not emitted from the endoscope system, the treatment or the surgery may not be performed smoothly.

On the other hand, even if the first light source unit 100 does not emit light due to a failure or the like, the endoscope system according to an embodiment of the present disclosure may emit light through the second light source unit 200, such that doctor may perform the treatment or the surgery more stably.

In addition, since there is no movement of the substrate 400, a drive system for moving the substrate 400 is not necessary, so that the endoscope system may be simply configured. On the other hand, as shown in FIG. 2, the first light source unit 100 may be arranged based on a central axis of the optical unit 300, and the second light source unit 200 may be placed to get out of the central axis.

The first light source unit 100 may be arranged based on the central axis of the optical unit 300 so as to supply a sufficient amount of light to the light guide unit 20 while the endoscope system of the present disclosure is operating normally.

On the other hand, when an abnormal operation that the first light source unit 100 does not emit light is accomplished, the substrate 400 does not move, such that the second light source unit 200 may provide an amount of light that can respond to the abnormal operation of the endoscope system although it stray out of the central axis.

As shown in FIG. 3, the substrate 400 may include a first substrate 410 and a second substrate 430. The first light source unit 100 may be installed in the first substrate 410 and the second light source unit 200 may be installed in the second substrate 430.

When the first light source unit 100 is not operated normally, the first substrate 410 may be separated from the second substrate 430 to be replaced with a new first substrate 410 in the maintenance/repair procedure of the endoscope system.

The first substrate 410 may be pressed in the hole of the second substrate 430, but the combination and the separation of the first substrate 410 and the second substrate 430 may be implemented through various configurations.

Meanwhile, FIG. 4 and FIG. 7 illustrate an endoscope system according to a second embodiment of the present disclosure. As shown in FIG. 4 and FIG. 7, the endoscope system according to a second embodiment of the present disclosure may include the first light source unit 100, the second light source unit 200, the optical unit 300, a driver 500, and the light guide unit 20.

The first light source unit 100 and the second light source unit 200 may be installed on the substrate 400. The first light source unit 100 and the second light source unit 200 may emit, as if white light, a light of various wavelengths such as visible light, ultraviolet rays, and infrared rays.

The light of the first light source unit 100 may pass through the optical unit 300. Since the optical unit 300 is described above in detail, an explanation thereof is omitted.

The driver 500 may move the substrate 400 so that the light of the second light source unit 200 may pass through the optical unit 300 when the first light source unit 100 does not emit light. The driver 500 may be connected with a drive shaft, and the drive shaft may be connected with the substrate 400. Accordingly, the driver 500 may rotate the substrate 400 through the drive shaft, and, for this purpose, may include a motor.

The light guide unit 20 may guide the light of the first light source unit 100 or the second light source unit 200 which has passed through the optical unit 300 into the inside of the target object.

As described above, when the first light source unit 100 is unable to perform a normal operation, the driver 500 may move the substrate 400 such that the light of the second light source unit 200 may pass through the optical unit 300. Thus, a stable operation of the endoscope system may be achieved.

The method of moving the substrate 400 may include various schemes such as a rotation scheme and a sliding scheme. The driver 500 of the endoscopic system of FIG. 4 may operate according to a rotation scheme, and the driver 500 of the endoscopic system of FIG. 7 may operate according to a sliding scheme.

The rotation scheme is described first and then the sliding scheme is described.

As shown in FIG. 4, when the first light source unit 100 emit light, the first light source unit 100 may be arranged along the optical unit 300 and a central axis. At this time, the central axis may be a central axis of the optical unit 300.

When the first light source unit 100 does not emit light due to failure or the like, the driver 500 may rotate the substrate 400, so that the second light source unit 200 may be arranged along the optical unit 300 and the central axis.

In the meantime, as shown in FIG. 5, the endoscope system according to a second embodiment of the present disclosure may further include an additional substrate 600, and a third light source unit 700 and a fourth light source unit 800 which are installed in the additional substrate 600.

The third light source unit 700 and the fourth light source unit 800 may emit the light of a different wavelength from the first light source unit 100 and the second light source unit 200. For example, when the first light source unit 100 and the second light source unit 200 emit a white light, the third light source unit 700 and the fourth light source unit 800 may emit ultraviolet rays or infrared rays.

When the third light source 700 does not emit light, the driver 500 of FIG. 5 may move the additional substrate 600 so that the light of the fourth light source unit 800 may pass through the optical unit 300, and the light of the third light source unit 700 or the fourth light source 800 may pass through the optical unit 300 through a groove (400a) or a hole (400a) formed in the substrate 400.

At this time, the first light source unit 100 and the third light source unit 700 may emit a light of a different wavelength simultaneously, and, when the first light source unit 100 and the third light source unit 700 do not emit light, the second light source unit 200 and the fourth light source unit 800 may emit a light of a different wavelength simultaneously.

When the first light source unit 100 and the third light source unit 700 emit a light of different wavelength simultaneously, or when the second light source unit 200 and the fourth light source unit 800 emit a light of different wavelength simultaneously, a composite image which is obtained by synthesizing an image corresponding to each wavelength may be displayed through a display unit.

In the case of the endoscope system of FIG. 5, a single rotation shaft may be connected to the substrate 400 and the additional substrate 600. On the other hand, a rotation shaft of the substrate 400 and a rotation shaft of additional substrate 600 may be separately provided.

In the meantime, the endoscope system of FIG. 6 may also further include the substrate 600, and the third light source unit 700 and the fourth light source unit 800 which are installed in the additional substrate 600.

The first light source unit 100 and the third light source unit 700 that emit light may be located closer to the central axis of the optical unit 300 in comparison with the second light source unit 200 and the fourth light source unit 400 respectively.

At this time, when the first light source unit 100 does not emit light, the driver 500 may rotate the substrate 400 so that the second light source unit 200 may be located closer to the central axis in comparison with the first light source unit 100.

In addition, when the third light source unit 700 does not emit light, the driver 500 may rotate the additional substrate 600 so that the fourth light source unit 800 may be located closer to the central axis in comparison with the third light source unit 700.

Accordingly, light may pass through the optical unit 300 as much as possible in the state in which the first light source unit 100 to the fourth light source unit 800 are not arranged in the central axis of the optical unit 300.

The wavelength of the light of the first light source unit 100 may be different from the wavelength of the light of the third light source unit 700 and the fourth light source unit 800, and the wavelength of the light of the second light source unit 200 may also be different from the wavelength of the light of the third light source unit 700 and the fourth light source unit 800.

In the endoscope system of FIG. 6, the first light source unit 100 and the third light source unit 700 may emit light of a different wavelength simultaneously, and, when the first light source unit 100 and the third light source unit 700 does not emit light, the second light source unit 200 and the fourth light source unit 800 may emit light of a different wavelength simultaneously.

As shown in FIG. 5 and FIG. 6, the driver 500 may be connected to the rotation axis of the substrate 400 and the additional substrate 600 to rotate the substrate 400 and the additional substrate 600.

Next, the sliding scheme which is different from the rotation scheme is described.

As shown in FIG. 7, when the first light source unit 100 emits light, the first light source unit 100 may be arranged along the optical unit 300 and the central axis. When the first light source unit 100 does not emit light, the driver 500 may move the substrate 400 linearly such that the second light source unit 200 may be arranged along the optical unit 300 and the central axis.

In the case of the rotation scheme, the driver 500 may be connected to the rotation axis of the substrate 400 or the additional substrate 600. In the case of the sliding scheme, the driver 500 may move the substrate 400 by making a piston to perform a linear motion, but it is not limited thereto, and may apply various structures for the linear motion of the substrate 400.

Next, a controller according to the first embodiment and the second embodiment of the present disclosure is described with reference to the drawings.

As shown in FIG. 8 and FIG. 9, the endoscope system according to the first embodiment of the present disclosure may further include a controller 900.

As shown in FIG. 8, a power supply (PWR) may supply power to the first light source unit 100 and the second light source unit 200, and the controller 900 may sense whether power is supplied to the first light source unit 100.

For example, when the first light source unit 100 includes an LED, the controller 900 may sense a current supplied to the first light source unit 100.

When the first light source unit 100 is unable to emit light due to failure, power may not be supplied to the first light source unit 100. Accordingly, the controller 900 may turn a switching unit (S) on by sensing the stop of the supply of the power.

At this time, one end of the switching unit (S) may be connected with the second light source unit 200, and the other end of the switching unit S may be connected with the power supply (PWR), but the connection relation of the switching unit (S) is not limited thereto and may be changed according to a design.

Accordingly, the second light source unit 200 may be supplied with power and may emit light.

Meanwhile, as shown in FIG. 9, the first light source unit 100 which is supplied with power to emit light may be connected to a first resistor R1, and the second light source unit 200 may be connected to a second resistor R2 have. At this time, the resistance value of the first resistor R1 may be smaller in comparison with the second resistor R2.

Since the resistance value of the first resistor R1 is smaller in comparison with the second resistor R2, a current flowing in the first light source unit 100 may be larger than a current flowing in the second light source unit 200.

At this time, the ratio of the resistance value of the first resistor R1 and the second resistor R2 may be set in such a manner that the first light source unit 100 emits light in a normal operation state, and the second light source unit 200 does not emit light.

When the first light source unit 100 is unable to emit light due to failure, the resistance of the first light source unit 100 may be largely increased, such that the magnitude of current flowing into the first resistor R1 may be decreased or the flow of the current may be stopped and the magnitude of the current flowing into the second resistor R2 may be increased.

When the first light source unit 100 is unable to emit light, the power of the power supply (PWR) may be supplied to the second light source unit 200 through the second resistor R2, and thus the second light source unit 200 may emit light.

As shown in FIG. 10 to FIG. 13, the endoscope system according to the second embodiment of the present disclosure may further include the controller 900.

As shown in FIG. 10 to FIG. 13, when at least one of the first light source unit 100 and the third light source unit 700 is unable to emit light, the power of the power supply (PWR) may not be supplied to at least one of the first light source unit 100 and the third light source unit 700.

Accordingly, the controller 900 may sense the stop of the supply of power to the at least one of the first light source unit 100 and the third light source unit 700, and, by controlling the switching unit (S), may supply the power of the power supply (PWR) to the second light source unit 200 when the supply of power to the first light source unit 100 is stopped, and may supply the power of the power supply (PWR) to the fourth light source unit 800 when the supply of power to the third light source unit 700 is stopped.

That is, as shown in FIG. 10 and FIG. 11, the power of the power supply (PWR) may be supplied to the first light source unit 100 and the third light source unit 700, and the controller 900 may check whether the power of the power supply (PWR) is supplied to the first light source unit 100 and the third light source unit 700.

In FIG. 10, the first light source unit 100 and the third light source unit 700 may receive the power of the power supply (PWR) through a wire, and the first light source unit 100 and the third light source unit 700 of FIG. 11 may receive the power of the power supply (PWR) through a separate wire.

For example, when the first light source unit 100 and the third light source unit 700 include a LED, the controller 900 may sense the current supplied to the first light source unit 100 and the third light source unit 700.

When the first light source unit 100 is unable to emit light due to failure, the power of the power supply (PWR) may not be supplied to the first light source unit 100 and the third light source unit 700. Accordingly, the controller 900 may turn the switching unit (S) on by sensing the stop of the supply of the power.

At this time, as shown in FIG. 10, one end of the switching unit (S) may be connected with the second light source unit 200 and the fourth light source unit 800, and the other end of the switching unit (S) may be connected with the power supply (PWR).

Accordingly, when the first light source unit 100 and the third light source unit 700 are unable to emit light, the switching unit (S) may be turned on according to the control of the controller 900 such that the second light source unit 200 and the fourth light source unit 800 may be supplied with the power of the power supply (PWR) to emit light.

At this time, the controller 900 may output a driving control signal for moving the substrate 400 or the additional substrate 600 to the driver 500.

Alternatively, as shown in FIG. 11, the switching unit (S) may include a first switch (sw1) and a second switch (sw2). One end and the other end of the first switch (sw1) may be connected with the second light source unit 200 and the power supply (PWR) respectively, and one end and the other end of the second switch (sw2) may be connected with the fourth light source unit 800 and the power supply (PWR) respectively.

The connection relation of the switching unit (S) is not limited thereto and may be changed according to the design. For example, the number of switches included in the switching unit (S) may be changed according to the number of the second light source unit 200 and the fourth light source unit 800.

Accordingly, when at least one of the first light source unit 100 and the third light source 700 is unable to emit light, the controller 900 may sense that the power of the power supply (PWR) is not supplied to at least one of the first light source unit 100 and the third light source unit 700.

Based on the sensing result, the controller 900 may turn on at least one of the first switch (SW1) and the second switch (SW2) to supply the power of the power supply (PWR) to at least one of the second light source unit 200 and the fourth light source unit 800.

At this time, the controller 900 may output a driving control signal for moving the substrate 400 or the additional substrate 600 to the driver 500.

Meanwhile, as shown in FIG. 12, the first light source unit 100 and the third light source unit 700 may be connected to the first resistor R1, and the second light source unit 200 and the fourth light source unit 800 may be connected to the second resistor R2.

At this time, the resistance value of the first resistor R1 may be smaller than that of the second resistor R2. At this time, the first light source unit 100 and the second light source unit 200 may be installed on the substrate 400 one by one, and the third light source unit 700 and the fourth light source unit 800 may be installed on the additional substrate 600 one by one.

Since the resistance value of the first resistor R1 is smaller than the second resistor R2, the current flowing in the first light source unit 100 or the third light source unit 700 may be greater than the current flowing in the second light source unit 200 or the fourth light source unit 800.

At this time, the ratio of the resistance value of the first resistor R1 and the second resistor R2 may be set in such a manner that the first light source unit 100 or the third light source unit 700 emits light in a normal operation state, and the second light source unit 200 or the fourth light source unit 800 does not emit light.

When the first light source unit 100 and the third light source unit 700 are unable to emit light due to failure or damage, the resistance of the first light source unit 100 and the third light source unit 700 may be largely increased, such that the magnitude of the current flowing into the first resistor R1 may be decreased and the magnitude of the current flowing into the second resistor R2 may be increased.

Thus, the second light source unit 200 and the fourth light source unit 800 may emit light. That is, when the first light source unit 100 and the third light source unit 700 are unable to emit light, the power of the power supply (PWR) may be supplied to the second light source unit 200 and the fourth light source unit 800 through the second resistor R2.

The controller 900 may sense the magnitude of the current flowing in the first resistor R1 and the second resistor R2 and may output a drive control signal to the driver 500 so that it is possible to move the substrate 400 or the additional substrate 600.

Meanwhile, as shown in FIG. 13, the cross-sectional shape of the substrate 400 of FIG. 1 may be recessed with respect to the optical unit 300. Accordingly, even if the second light source unit 200 is not arranged in the central axis of the second light source unit 200, light may be inputted to the optical unit 300 as much as possible.

Next, the endoscope system according to a third embodiment of the present disclosure is described with reference to the drawings.

FIG. 14 to FIG. 16 illustrate a first light source unit and a second light source unit of an endoscope system according to a third embodiment of the present disclosure, and omit the optical unit 300 for the convenience of explanation.

The endoscope system according to the third embodiment of the present disclosure may include the first light source unit 100, the second light source unit 200, the optical unit 300, and the light guide unit 20.

The first light source unit 100 may be installed on the substrate 400, and may be provided with a first terminal 150.

The second light source unit 200 may be installed on the substrate 400 and may be provided with a second terminal 250 in a non-boundary area which is not a boundary area with the first light source unit 100 and may emit light when the first light source unit 100 does not emit light.

At this time, the first terminal 150 and the second terminal 250 may include a positive (+) electrode and a negative (−) electrode.

Like the comparative example of FIG. 17 which is different from the third embodiment of the present disclosure, when the first terminal 150 and the second terminal 250 exist in the boundary area of the first light source unit 100 and the second light source unit 200, it can be seen that a gap (G) between the first light source unit 100 and the second light source unit 200 increases in comparison with the third embodiment of the present disclosure.

Unlike the above comparative example, the third embodiment of the present disclosure may reduce the gap between the first light source unit 100 and the second light source unit 200 as the first terminal 150 and the second terminal 250 do not exist in the boundary area of the first light source unit 100 and the second light source unit 200. Thus, the size of the substrate 400 may be reduced, and the light emitting unit 10 may also be reduced.

The light of the first light source unit 100 and the second light source unit 200 may pass through the optical unit 300. The light guide unit 20 may guide the light which passed through the optical unit 300 into the inside of a target object. Since the optical unit 300 and the light guide unit 20 are described in detail in the above through the first embodiment and the second embodiment, the description thereof is omitted.

Meanwhile, the first light source unit 100 and the second light source unit 200 may include total n partial light sources, and, when the first light source unit 100 includes m (m<n, m and n is a natural number) partial light sources, the second light source unit 200 may include partial light source which is equal to or greater than one and equal to or less than n−m.

The endoscope system of FIG. 14, FIG. 15, and FIG. 16 may have two (=n), three (=n), and four (=n) total partial light sources, respectively. In addition, the first light source unit 100 of FIG. 15, FIG. 16, and FIG. 17 may have one (=m), two (=m), and two (=m) total partial light sources, respectively.

When n=3 and m=1, the partial light sources of the second light source unit 200 may be one or two.

In addition, when n=4 and m=1, the partial light source of the second light source unit 200 may be one, two, or three. When m=3, the partial light source of the second light source unit 200 may be one.

Thus, the number of partial light sources of the first light source unit 100 and the second light source unit 200 may be changed depending on the design.

Meanwhile, the first light source unit 100 may be arranged along the central axis of the optical unit 300, and the second light source unit 200 may deviate from the central axis. For example, in the case in which the first light source unit 100 and the second light source unit 200 include a single partial light source respectively, when the partial light source of the first light source unit 100 is arranged on the central axis, the partial light source of the second light source unit 200 may be disposed on the substrate 400 in a different location from the partial light source of the first light source unit 100, such that it deviates from the central axis.

Thus, since the second light source unit 200 deviates from the central axis, even if the light amount transmitted to the light guide unit 20 is reduced, a clinician may perform a response in accordance with the abnormal operation of the endoscope system such as the failure of the first light source unit 100.

In addition, the number of partial light sources of the second light source unit 200 is set to be greater than the number of partial light sources of the first light source unit 100, it is possible to compensate the reduced amount of light caused by the disposition deviated from the central axis.

Meanwhile, as shown in FIG. 18, the first light source unit 100 and the second light source unit 200 may further include an additional optical unit 350 covering a light source mounted on the substrate 400. The light source may be LED, but it is not limited thereto. The additional optical unit 350 may be implemented by a resin, but it is not limited thereto. A radiator (HR) may be arranged between the light source and the substrate 400.

When the cross-sectional shape of the additional optical unit 350 may be curved or flat with respect to the direction of light. For example, it may be convex as shown in (a) of FIG. 19 or, on the contrary, may be concave, and may be flat as shown in (b) of FIG. 19.

In addition, the additional optical unit 350 may perform the function of the Fresnel lens as shown in (c) of FIG. 19.

The progress direction of the light may be controlled according to the design of the endoscope system by variously setting the shape of the additional optical unit 350. FIG. 20 is a block diagram illustrating an endoscope system according to embodiments of the present disclosure. As shown in FIG. 20, the endoscope system according to an embodiment of the present disclosure may include an endoscope 50 which can observe the light of a specific wavelength, an image signal processing unit 40 for driving the endoscope 50 and performing a signal processing of an image picked up by the endoscope 50, and a display unit 60 for displaying the pickup image of the target object.

The endoscope 50 may include a flexible or rigid insertion unit 50a which is inserted into the target object where light hardly reaches, a handle 25 provided to the insertion unit 50a, and a universal cord unit 50c extended from the side part of the handle 25, and may be electrically connected to the image signal processing unit 40 through the universal cord unit 50c.

In addition, a main body unit of the endoscope 50 may be mainly configured of the insertion unit 50a and the handle 25, and the pickup image signal and the control signals may be transmitted to the image signal processing unit 40 through a cable 1a, 3a.

An image sensing unit 30 such as CMOS or CCD, a motion detection sensor 1 such as a gyro sensor or an acceleration sensor, and a forceps hole may be provided to the end of the insertion unit 50a. Since the forceps hole is well known, a description thereof is omitted.

The image sensing unit 30 may be connected to an image sensor driver through the cable 3a which bundled a plurality of signal wires 3a, and the motion detection sensor 1 may also be connected through the cable 1a.

The light guide 20 may be connected to the image signal processing unit 40 through the universal cord unit 50c in the insertion unit 30a. The light guide 20 may guide the light emitted from the light emitting unit 10 to output to the end of the insertion unit 50a.

The image signal processing unit 40 is described only for the components related to the image pickup, and a description of the other common components needed for driving is omitted.

The image signal processing unit 40 may include, at least, an image sensor driver, a gain amplifier, an analog-to-digital converter unit (ADC), a digital signal processing unit (DSP), a digital-to-analog converter unit (DAC), and a CPU.

The light emitting unit 10 may be driven by receiving power by the driver, and the driver may be controlled by the CPU.

The endoscopic system according to an embodiment of the present disclosure may generate a stable image as a second light source unit supplies a light when a first light source unit operates abnormally.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. An endoscope system comprising:
   a first light source unit which is installed on a substrate;
   a second light source unit which is installed on the substrate and which emits light when the first light source unit does not emit light;
   an optical unit through which the light of the first light source unit or the second light source unit passes;
   a light guide unit which induces the light which passed through the optical unit to the inside of a target object;
   an image sensing unit which senses the light reflected and reached from the target object and which converts the sensed light into an image signal; and
   an image signal processing unit which processes the image signal to display on a display unit,
   wherein the substrate includes a first substrate and a second substrate capable of being physically separated from the first substrate, and the first light source and the second light source are installed in the first substrate and the second substrate, respectively.

2. The endoscope system of claim 1, wherein the light of the second light source unit passes through the optical unit when the light of the first light source unit does not emit light.

3. The endoscope system of claim 1, wherein the first light source unit is arranged along a central axis of the optical unit, and the second light source unit is arranged to deviate from the central axis.

4. The endoscope system of claim 1, further comprising a controller which senses whether power is supplied to the first light source unit, and the controller turns a switching unit on by sensing a stop of the supply of the power to supply the power to the second light source unit, when the power is not supplied to the first light source unit.

5. The endoscope system of claim 1, wherein the first light source unit that is supplied with power to emit light is connected to a first resistor and the second light source unit is connected to a second resistor, the first resistor has a small resistance value in comparison with the second resistor, and the power is supplied to the second light source unit through the second resistor when the first light source unit does not emit light.

6. The endoscope system of claim 1, wherein a cross-sectional shape of the substrate is recessed with respect to the optical unit.

7. An endoscope system comprising:
   a first light source unit which is installed on a substrate, and which is provided with a first terminal;
   a second light source unit which is installed on the substrate and which is provided with a second terminal in a non-boundary area, the first light source and the second light source are not facing each other, wherein the second light source unit emits light when the first light source unit does not emit light;
   an optical unit through which the light of the first light source unit or the second light source unit passes;
   a light guide unit which induces the light which passed through the optical unit to the inside of a target object;
   an image sensing unit which senses the light reflected and reached from the target object and which converts the sensed light into an image signal; and
   an image signal processing unit which processes the image signal to display on a display unit,
   wherein the substrate includes a first substrate and a second substrate capable of being physically separated from the first substrate, and the first light source and the second light source are installed in the first substrate and the second substrate, respectively.

8. The endoscope system of claim 7, wherein the first light source unit and the second light source unit comprise total n light sources, and, when the first light source unit includes m (m<n, m and n is a natural number) light sources, the second light source unit includes light source which is equal to or greater than one and equal to or less than n−m.

9. The endoscope system of claim 7, wherein the first light source unit is arranged along a central axis of the optical unit, and the second light source unit is arranged to deviate from the central axis.

10. The endoscope system of claim 7, wherein the first light source unit and the second light source unit further comprise an additional optical unit covering a light source mounted on the substrate,
   and a cross-sectional shape of the additional optical unit is curved or flat with respect to a direction of a light.

11. The endoscope system of claim 7, wherein the first light source unit and the second light source unit further comprise an additional optical unit covering a light source mounted on the substrate, and the additional optical unit performs a function of a Fresnel lens.

12. The endoscope system of claim 7, wherein a cross-sectional shape of the substrate is recessed with respect to the optical unit.

\* \* \* \* \*